United States Patent [19]

Zagorski

[11] Patent Number: 4,723,546

[45] Date of Patent: Feb. 9, 1988

[54] APPARATUS FOR ARTHROSCOPIC SURGERY

[76] Inventor: Joseph B. Zagorski, 355 Marquesa Dr., Coral Gables, Fla. 33156

[21] Appl. No.: 875,181

[22] Filed: Jun. 17, 1986

[51] Int. Cl.[4] .............................................. A61B 17/32
[52] U.S. Cl. ................................ 128/305; 128/303 R; 128/329 R
[58] Field of Search ..................... 128/330, 20, 329 R, 128/305, 751, 753, 754, 303 R

[56] References Cited

U.S. PATENT DOCUMENTS

| | | | |
|---|---|---|---|
| 1,059,631 | 4/1913 | Popovics | 128/330 |
| 1,867,624 | 7/1932 | Hoffman | 128/305 X |
| 4,221,212 | 9/1980 | Miller | 128/330 X |
| 4,378,019 | 3/1983 | Yamada | 128/330 |
| 4,382,444 | 5/1983 | Malmin | 128/330 |
| 4,461,281 | 7/1984 | Carson | 128/305 X |
| 4,517,965 | 5/1985 | Ellison | 128/20 |

FOREIGN PATENT DOCUMENTS 1393068  5/1975  United Kingdom ................ 128/754

*Primary Examiner*—Michael H. Thaler
*Attorney, Agent, or Firm*—Larson and Taylor

[57] ABSTRACT

A method and apparatus for arthroscopic surgery provides a means for retaining loose tissue within a joint so that the tissue may be readily cut and removed from the joint. The apparatus comprises a harpoon-like shaft which is inserted into the body joint and the barb on the end of the shaft is engaged with the loose tissue within the joint. The shaft is then drawn outwardly slightly to tension the loose tissue so that it can be cut to permit the removal of the tissue from the joint. A cannula is slidable over the shaft and the end portion of the cannula is bevelled to fit beneath the barb. With the cannula engagable with the undersurface of the barb the device can be removed from the joint without engaging any adjacent tissue. The completely detached tissue may then be grasped and withdrawn through an opening into the joint.

4 Claims, 5 Drawing Figures

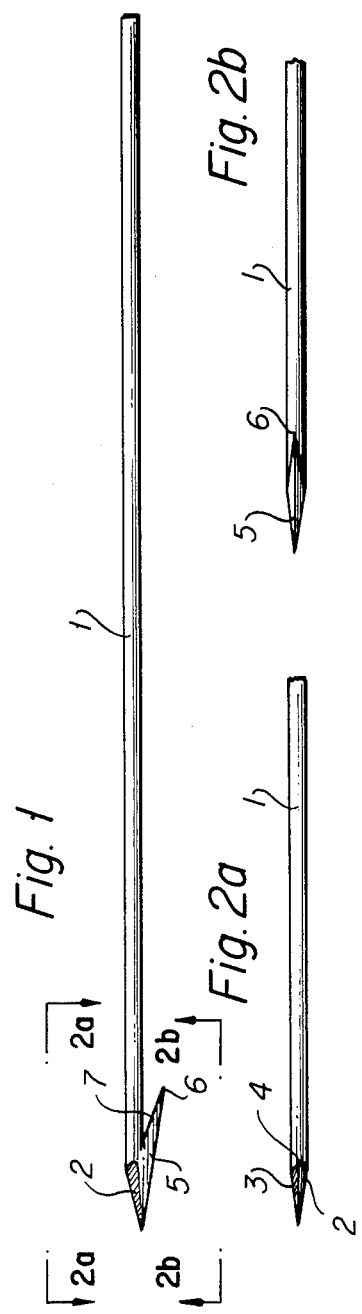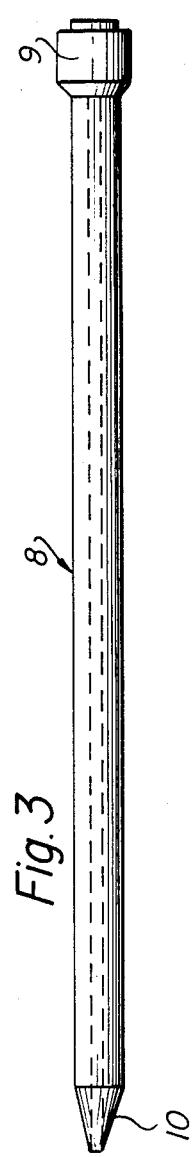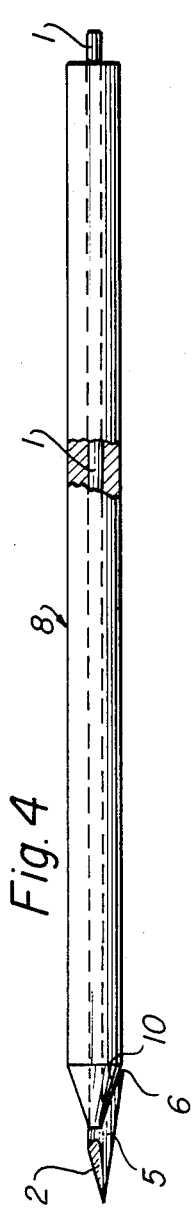

APPARATUS FOR ARTHROSCOPIC SURGERY

BACKGROUND OF THE INVENTION

The invention relates to a method and apparatus for removing tissue from a body joint wherein a specially designed hook on the end of a shaft engages the tissue to retain it in a tensioned state while it is being detached from the joint after which means is provided for releasing the tissue from the hook and withdrawing the hook from the joint.

In the practice of arthroscopic surgery it is a well known procedure to form an opening in a joint and to remove a meniscus from the joint. In arthroscopic surgery such procedures may be performed without making any standard large skin and tissue incisions. Typically the procedure is performed through small stab wounds through which arthroscopic instruments are inserted into the joint, such as the knee, and under direct visualization various procedures may be performed. It has been frequently difficult to cut loose tissue or a meniscus within a joint without making multiple stab wound incisions. In order to effectively cut such tissue in the past it has been frequently necessary to create additional openings in order to enable the surgeon to cut the tissue under tension. Obviously, it would be desirable to provide a method and apparatus which would ensure that loose tissue could be cut effectively through a minimal number of incisions and thus avoid the need for multiple wounds.

There have been devices in the prior art for removing objects from the body of a human which include a hook or the like. For example, U.S. Pat. No. 4,368,734 discloses a device for grasping a portion of the object to be removed and to bring the object into contact with a cutting surface for cutting the object to permit its removal. U.S. Pat. No. 3,817,250 discloses a surgical device which is used in emergency tracheostomy procedures. This device discloses a split needle with a collar which extends thereover and a cavity means in the collar to enable expansion of the needle. U.S. Pat. No. 3,624,747 discloses a surgical instrument having a hook-like portion on the end thereof for the purpose of rupturing the amniotic membrane. This device would not be suitable for arthroscopic surgery. U.S. Pat. No. 3,645,268 discloses a piercing evacuator having a hollow elongated body and a cutting head thereon with openings therethrough to permit discharge from an inner area to the exterior through a membrane such as the eardrum. The prior art is devoid of a disclosure of a surgical instrument suitable for arthroscopic surgery to retain loose tissue within a knee joint and provided with means to permit removal of the instrument from the joint without engagement with other tissue.

SUMMARY OF THE INVENTION

The present invention provides a method and apparatus for removing, stabilizing or retracting loose tissue in a joint during arthroscopic surgical procedures wherein an elongated shaft is provided with a barb or hook-like projection on the proximal end thereof which is engageable with the loose tissue. The end of the shaft is formed with bevel faces to form a cutting edge similar to a conventional surgical needle. The face of the end of the needle opposite to the cutting edge is formed with a rearwardly extending tapered projection forming a barb and forming a substantially V-shaped recess between the barb and the needle shaft. A cannula or sheath is provided which has a tapered end portion, the aperture in the cannula fitting over the needle shaft in easy sliding relationship. When the cannula is slid over the shaft to a position wherein the end of the cannula engages the inner end portion of the barb at its point of attachment to the shaft the bevelled end portion of the cannula lies adjacent and in engagement with the inner face of the barb along its entire length so as to render the barb inoperative. Thus, the cannula and shaft may be withdrawn from a puncture with engagement of tissue by the barb.

In use the barbed needle is inserted into a knee joint and a torn meniscal fragment may be speared by the cutting edge of the needle and the barb, much like a fish hook, retaining the meniscal tissue. By pulling on the needle the barb will be adequately engaged within the meniscus and may maintain tension on the meniscus while a knife or other cutting instrument is used to trim the torn meniscal fragment. When the fragment is completely cut the cutting instrument is withdrawn from the stab wound incision. A conventional meniscus grasper or other grasping instrument may then be inserted to grasp the loose meniscal fragment. The barbed needle may then be pushed inwardly slightly and the cannula slid over the shaft of the barbed needle so as to release the meniscus from the barbed needle. The cannula and the needle may then be withdrawn at one time together. The grasper which is holding the loose meniscus fragment may then be used to pull the entire torn fragment out through the stab wound.

An object of the present invention is to provide a method and apparatus to facilitate cutting and removing loose tissue during arthroscopic surgical procedures.

Another object of the present invention is to provide a barbed needle for grasping loose tissue within a knee joint and for retaining the loose tissue during cutting operation and provided with means for releasing the tissue from the barbed needle.

Another object of the present invention is to provide a method to retract tissue within a joint, e.g. the fat pad, during arthroscopic procedures.

Other objects and many of the attendant advantages will become apparent upon consideration of the following detailed specification in connection with the accompanying drawings wherein:

BRIEF DESCRIPTION OF THE DRAWINGS

FIG. 1 is a side elevation showing the shaft having a cutting end and barb thereon;

FIG. 2a is a top plan view of the shaft shown in FIG. 1 along the line 2a—2a;

FIG. 2b is a bottom plan view of the shaft shown in FIG. 1 along the line 2b—2b;

FIG. 3 is a side elevational view of the cannula; and

FIG. 4 is a side elevational view showing the cannula in position over the shaft in engagement with the barb on the end of the shaft.

DETAILED DESCRIPTION OF THE PREFERRED EMBODIMENT

Referring now more specifically to the drawings wherein like numerals indicate like parts throughout the several views there is shown at 1 in FIG. 1 a shaft which may be made of a metal or any suitable material generally used for surgical needles. The diameter of the shaft is in the range of 0.5 to 2 millimeters and the length may vary dependent upon the tissue with which it is used but in general is in the range of 10 to 20 centimeters. The end of the shaft 1 is provided with bevelled cutting surfaces as shown at 2 and 3 in FIG. 2 to form a cutting edge extending from the tip of the shaft 1 on one side of the shaft to a point 4 spaced from the end of the shaft at the opposite side of the shaft. A barb-like projection 5 having beveled side faces as shown in FIG. 2b extends from the tip of the shaft 1 rearwardly and projects outwardly to a pointed tip 6 so as to form a substantially V-shaped opening 7 between the inner edge of the barb 5 and the surface of the shaft 1.

As shown in FIG. 3 there is provided a cannula or sheath 8 which may be made of plastic material or may be of metal. The cannula or sheath 8 has a bore therein centrally located which is slightly larger than the diameter of the shaft 1 so that the cannula may be easily slid over the shaft 1. The distal end of the cannula is provided with a hub 9 which may be grasped by the surgeon in use. The proximal end 10 of the cannula 8 is substantially cone-shaped or bevelled so that when the cannula 8 is slid completely over the shaft 1 the proximal end of the cannula engages the end of the V-shaped recess 7 formed between the barb 5 and the shaft 1. It can be seen that in this position the bevelled end portion 10 of the cannula 8 engages the inner face of the barb 5 so that the end point 6 of the barb is in alignment with or recessed beneath the outer surface of the cannula 8. Thus, there is no possibility of the barb 5 becoming engaged with body tissue a the shaft and cannula are moved outwardly of an incision.

In use in arthroscopic surgery the shaft 1 is inserted through a puncture in the skin and into a joint, for example. After the loose tissue to be removed is cut by the bevelled cutting edges on the shaft 1 and barb 5 and the proximal end of the instrument is passed through the tissue, a meniscus or other loose tissue is firmly engaged with the instrument by drawing the shaft back out of the puncture site to engage the point 6 of barb 5 with the meniscus. By drawing the shaft further outwardly the meniscus is tensioned so as to facilitate using a separate cutting instrument to cut the meniscus free for removal. The meniscus may then be grasped by a separate clamping or grasping instrument and the shaft 1 can be moved inwardly to release the meniscus from the barb 5. The cannula 8 is then slid over the shaft 1 to a position as shown in FIG. 4 wherein the barb 5 and end point 6 of the barb are prevented from engaging any tissue as the shaft 1 and cannula are withdrawn through the incision. The meniscus may then be removed by withdrawing the grasper or other holding instrument through the incision. The use of the presently disclosed instrument facilitates the cutting of loose tissue during arthroscopic surgery and enables a surgeon to carry out a complete operation effectively and efficiently through a small incision minimizing the need for additional incisions.

Obviously many modifications and variations of the present invention are possible in light of the above teachings. What is claimed as new and is desired to be secured by Letters Patent is:

1. A surgical instrument for retaining tissue in a body joint or the like comprising an elongated shaft, means projecting from one end of said shaft for engaging and retaining body tissue, said means including a barb projecting rearwardly and outwardly from one end of said shaft, a substantially V-shaped recess formed between said barb and the surface of said shaft, and means on said shaft for rendering said engaging and retaining means inoperative, said last named means including a cannula slidable on said shaft, said cannula having a cone shaped end portion, the cone shaped end portion of said cannula fitting within the V-shaped recess so as to prevent engagement of the barb with body tissue when the surgical instrument is being removed from the body joint.

2. A surgical instrument according to claim 1 and further including a cutting edge on the end portion of said elongated shaft to permit cutting of tissue in a body joint prior to engagement of the tissue with said engaging and retaining means.

3. A surgical instrument according to claim 1 wherein the outer surface of the cannula is substantially in alignment with the outer end point of the barb when the cone shaped end portion of the cannula is in engagement with the barb in the V-shaped recess.

4. A surgical instrument according to claim 3 wherein said cannula has an enlarged hub on the end of the cannula remote from the cone shaped end portion.

* * * * *